United States Patent
Carlucci

(10) Patent No.: US 7,100,439 B2
(45) Date of Patent: Sep. 5, 2006

(54) BALANCE CONTROL SYSTEM FOR WEIGHT SCALES

(75) Inventor: Vito James Carlucci, Stratford, CT (US)

(73) Assignee: Conair Corporation, Stamford, CT (US)

( * ) Notice: Subject to any disclaimer, the term of this patent is extended or adjusted under 35 U.S.C. 154(b) by 205 days.

(21) Appl. No.: 10/308,993

(22) Filed: Dec. 2, 2002

(65) Prior Publication Data

US 2004/0118617 A1    Jun. 24, 2004

(51) Int. Cl.
*A61B 5/00* (2006.01)
*G01G 19/00* (2006.01)

(52) U.S. Cl. .................. 73/172; 177/199; 177/200; 600/587; 600/592; 178/18.05

(58) Field of Classification Search ............. 178/18.05; 177/199–200; 600/587, 592; 73/172
See application file for complete search history.

(56) References Cited

U.S. PATENT DOCUMENTS

| | | | | |
|---|---|---|---|---|
| 2,374,105 A | * | 4/1945 | Kraus | 73/172 |
| 2,653,475 A | * | 9/1953 | Kraus | 73/172 |
| 3,657,475 A | * | 4/1972 | Peronneau et al. | 178/18.05 |
| 3,826,145 A | * | 7/1974 | McFarland | 600/595 |
| 4,047,427 A | * | 9/1977 | Young | 73/862.041 |
| 4,558,757 A | * | 12/1985 | Mori et al. | 178/18.05 |
| 4,805,637 A | * | 2/1989 | Walthert | 600/587 |
| 4,848,477 A | * | 7/1989 | Oldendorf et al. | 177/25.14 |
| 5,276,432 A | * | 1/1994 | Travis | 340/573.4 |
| 5,474,327 A | * | 12/1995 | Schousek | 280/735 |
| 5,750,937 A | * | 5/1998 | Johnson et al. | 177/25.11 |
| 6,437,257 B1 | * | 8/2002 | Yoshida | 177/199 |
| 6,852,086 B1 | * | 2/2005 | Atlas et al. | 600/595 |
| 2004/0163855 A1 | * | 8/2004 | Carlucci | |

FOREIGN PATENT DOCUMENTS

JP    57-163826    * 10/1982    ................. 177/200

* cited by examiner

*Primary Examiner*—Randy W. Gibson
(74) *Attorney, Agent, or Firm*—Lawrence Cruz; Steven A. Barnei

(57) ABSTRACT

The present invention is directed to a weight scale having a balance control system that detects unequal load distribution to the scale's load sensors and produces an output signal that enables the user to re-distribute weight until a predetermined level of balance is achieved. Various load sensors are positioned in an array within the scale and are in communication with a controller that receives signals from the sensors indicative of relative load applied to each. The controller generates a signal that is displayed or emitted to the user indicative of the position of the user's center of gravity relative to the sensors.

4 Claims, 2 Drawing Sheets

BALANCE CONTROL SYSTEM FOR WEIGHT SCALES

CROSS-REFERENCE TO RELATED APPLICATIONS

None.

BACKGROUND OF THE INVENTION

1. Field of the Invention

The present invention relates to weight scales and, more specifically, to a balance control system that detects load distribution on the scale and provides an output signal to a user to indicate whether or not the user should re-position or shift weight in order to more equally distribute load and, thus, optimize scale accuracy.

2. Description of Related Art

Various known weight scales generally provide an upper platform for the user to stand on, having load detection cells positioned beneath. The load from the weight of the user is transmitted from the platform to the load detection cells which are mounted to a base. The load on the cells is measured by the cells and communicated to a controller which causes an output display of the user's weight. The load detection cells are usually positioned in an evenly spaced array in an effort to position them whereby the load of the user is likely to be evenly distributed. This requires anticipation of precisely where the user is likely to stand on the scale and of how the user will distribute his or her weight in terms of distribution between front and back of the foot as well as right-vs.-left foot. The resultant scale reading is sometimes inaccurate because each user may stand on the scale in a different position and with different weight distribution, and each user has different size feet.

OBJECTS OF THE INVENTION

It is an object of the present invention to provide a weight scale that overcomes the above-identified shortcomings of known scales. These and other objects of the present invention are achieved by the embodiments described below.

BRIEF SUMMARY OF THE INVENTION

The present invention is directed to a weight scale having a balance control system that detects unequal load distribution to the scale's load cells and produces an output signal that enables the user to re-distribute weight until a predetermined level of balance is achieved.

DETAILED DESCRIPTION OF THE INVENTION

Figure 1:
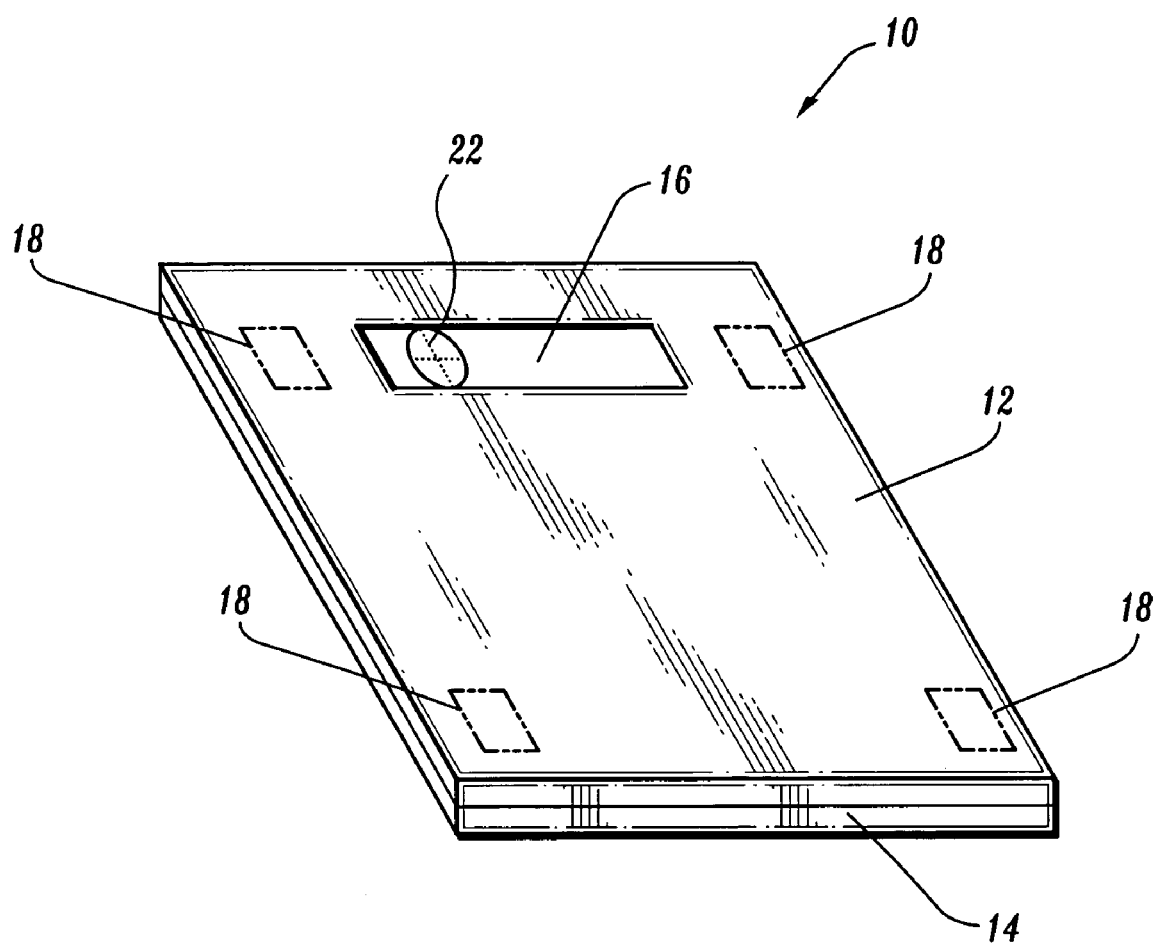
FIG. 1 is a schematic, perspective view of a weight scale according to the present invention.

Referring to FIG. 1, a weight scale (10) includes an upper platform (12), a base (14), a display screen (16), and a plurality of load detection cells (18) (shown in phantom) positioned between the platform (12) and the base (14). The cells (18) are mounted between the platform (12) and the base (14) in such a way that the load of the user's weight on the platform (12) will be transmitted directly to the cells (18). The cells (18) may be of the type generally known in the art, which generally include a deflectable member (not shown) through which electric current is passed. When the deflectable member flexes under load, it resistance properties are altered, and the change is monitored by measuring current flow. This is translated into a weight reading displayed to the user on the display screen (16).

Figure 2:
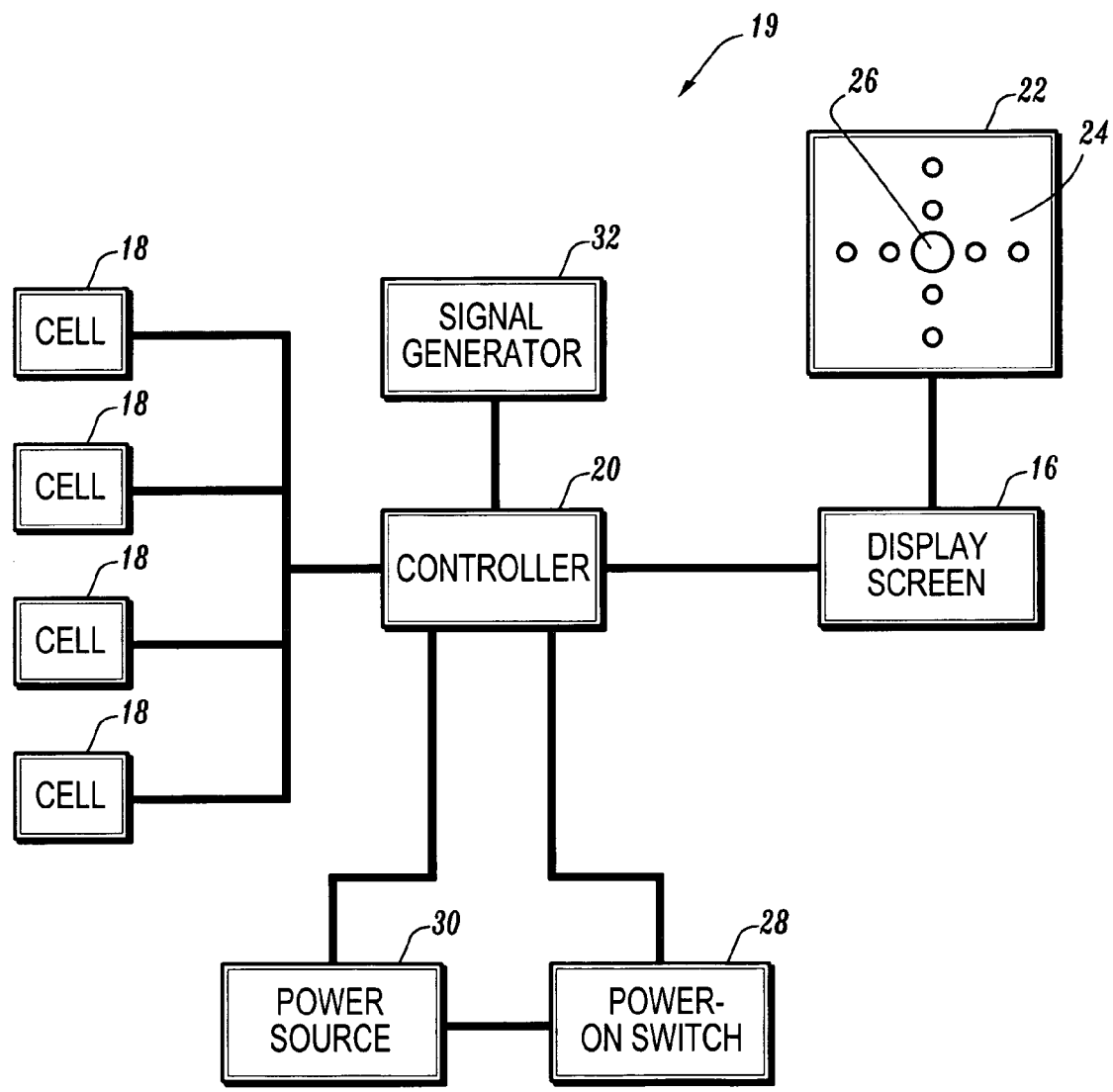
FIG. 2 is a schematic diagram of a balance control system for weight scales according to the present invention.

Referring to FIG. 2, a schematic diagram of the balance control system (19) for a weight scale (10) according to the present invention shows four load detections cells (18). A computer controller (20), of the type generally known, communicates with the cells (18) to process load signals therefrom, compare the signals, and provide an output signal to the display screen (16) that indicates to the user whether or not the user's weight is evenly distributed.

Various types of display or audible signal configurations may be used to indicate to the user whether or not a state of equal weight distribution, or balance, is present. In the preferred embodiment, as shown in FIG. 2, a balance display (22) may be included in or separate from the display screen (16). The balance display (22) may include an array of lights (24) arranged symmetrically and having a central light (26).

In the preferred embodiment, as shown in FIG. 1, the load detection cells (18) are arranged in a square configuration such that if a user stands so that his center of gravity is in the center of the scale platform (12), the load caused by the user's weight will be equally distributed and supported by each of the four load detection cells (18). It is understood that any number of cells (18) more than two may be used.

When the user stands on the platform (12), the lights on the balance display (22) light up in an array indicative of the user's center of gravity position. For example, if the user's weight is centered with respect to the four cells (18), only the central light (16) will be lit. If the user is leaning or standing too much to the right, both lights (24) to the right hand side of the central light (26) will light up. As the user leans or stands more to the left, only the single light directly to the right of the central light (26) will light up, thus indicating that the user's weight is shifted more toward the center. When the user finally shifts his weight to the center, only the central light (26) is lit.

Different balance indicators can be used in place of the precise embodiment described above. For instance, a different array of lights can be used, and the lighting or un-lighting sequences can be reversed depending on preference. Another way of indicating balance is to provide an audible signal that signals when the user's weight is centered, when it is not, and/or to which direction the user should re-position to achieve balance.

Operation of the above-described preferred embodiment will now be described. Initially, when the scale is at rest, the scale is not powered. When the user desires to use the scale, the user merely taps the platform (12). Tapping the platform (12) triggers a power-on switch (28) of the type generally known which activates a power source (30), such as a battery-powered pack. Alternatively, a manually activated power-on switch (not shown) may be provided for hand manipulation or toe-touch manipulation. After the scale (10) is powered on, the scale performs a self-zeroing routine as is known in various existing scales. The self-zeroing routine generally signals to the controller that in the instant condition, the weight output on the display screen should read zero.

Once the scale (10) has self-zeroed, the display screen will read "0", indicating to the user that the scale (10) is now ready for the user to stand on the scale. The user then steps onto the scale. The balance display (22) responds to the position of the user's center of gravity by lighting up accordingly, as described above, prompting the user to re-position or shift until the central light (26) illuminates. Optionally, the scale controller (20) may be programmed to not display the user's weight, thus displaying a blank screen or remaining at "0", until the user controller has indicated that the user's weight is centered. In lieu of, or in combination with, the visual signal, an audible signal may be produced by an audible output generator (32) that indicates relative position of the center of gravity and/or a balanced condition.

When the user's weight is sufficiently centered with respect to the load detection cells (18), the balance display (22) will indicate the balanced condition. A signal indicating that balance is achieved will prompt the controller (20) to activate the display screen (16) to display the user's weight in pounds or kilograms. When the user steps off of the scale (10), the controller (20) activates a time-out sequence to power-off the scale (10) after a predetermined period. When the scale (10) is tapped again, the operational procedure repeats.

The scale (10) may be provided with additional features such as a display clock and calendar, a radio and/or audible signaling device, and programmable sounds.

While the preferred embodiment has been herein described, it is understood that various modifications can be made without departing from the scope of the present invention.

What is claimed is:

1. A weight position sensor system for use with a scale for measuring the weight of an object, said scale comprising:
   a weight supporting surface for supporting an object to be weighed;
   three or more load detection sensors adapted to detect the presence of said object on said supporting surface;
   a controller adapted to receive a signal from said three or more load detection sensors indicative of the relative position of the center of gravity of said object with respect to the location of said three or more load detection sensors;
   an output signal generator adapted to generate a signal indicative of said relative position; and
   an electronic visual indicator adapted to display said signal indicative of said relative position in the form of an array of lights arranged symmetrically,
   wherein said electronic visual indicator further comprises a central light within said array of lights.

2. A system according to claim 1, wherein said output signal generator generates signals and displays corresponding visual signals in response to successive re-positioning of said object's center of gravity relative to said three or more load detection sensors.

3. A system according to claim 1, wherein said output signal generator generates an audible signal indicative of said relative position.

4. A scale for measuring the weight of an object, said scale comprising
   a weight supporting surface for supporting an object to be weighed;
   three or more load detection sensors adapted to detect the presence and weight of said object on said supporting surface;
   a controller adapted to receive a signal from said three or more load detection sensors indicative of the relative position of the center of gravity of said object with respect to the location of said three or more load detection sensors, and one or more signals indicative of the weight of said object;
   an output signal generator adapted to generate a signal indicative of the relative position and to generate a signal indicative of the weight of said object; and
   an electronic visual indicator adapted to display said signal indicative of said relative position of said object in the form of an array of lights arranged symmetrically and a central light within said array of lights.

* * * * *